US008172837B2

(12) United States Patent
Rothstein et al.

(10) Patent No.: US 8,172,837 B2
(45) Date of Patent: *May 8, 2012

(54) CLAMPING ABLATION TOOL AND METHOD

(75) Inventors: Paul T. Rothstein, Brooklyn Park, MN (US); David E. Francischelli, Brooklyn Park, MN (US); Terri Jean Cormack, Brooklyn Park, MN (US); Tom P. Daigle, Brooklyn Park, MN (US); Alison Lutterman, Minneapolis, MN (US); Roderick E. Briscoe, Brooklyn Park, MN (US); Steven C. Christian, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/814,992

(22) Filed: Jun. 14, 2010

(65) Prior Publication Data

US 2011/0071519 A1    Mar. 24, 2011

Related U.S. Application Data

(62) Division of application No. 11/143,399, filed on Jun. 2, 2005, now Pat. No. 7,758,576.

(60) Provisional application No. 60/576,356, filed on Jun. 2, 2004.

(51) Int. Cl.
*A61B 18/14* (2006.01)

(52) U.S. Cl. ............................................. 606/41; 606/50

(58) Field of Classification Search ................... 606/41, 606/50

See application file for complete search history.

(56) References Cited

U.S. PATENT DOCUMENTS

| | | | |
|---|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |

(Continued)

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

(Continued)

*Primary Examiner* — Lee Cohen

(57) ABSTRACT

Method and apparatus for ablating target tissue adjacent pulmonary veins of a patient. A clamping ablation tool can include an upper arm having an upper neck, a link assembly, and an upper actuator. The link assembly can include a distal electrode and a proximal electrode. The clamping ablation tool can include a lower arm that mates with the upper arm. The lower arm can include a lower neck, a distal jaw, and a lower actuator. The distal jaw can include a jaw electrode, and the lower actuator can control movement of the distal jaw.

6 Claims, 22 Drawing Sheets

U.S. PATENT DOCUMENTS

| | | |
|---|---|---|
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Sliwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |

| Patent No. | Date | Inventor(s) |
|---|---|---|
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,944 B1 | 9/2002 | Doshi et al. |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns |
| 6,527,767 B2 | 3/2003 | Wang et al. |
| 6,537,248 B2 | 3/2003 | Mulier |
| 6,539,265 B2 | 3/2003 | Hoey |
| 6,558,382 B2 | 5/2003 | Jahns |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,692,491 B1 | 2/2004 | Phan |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,758,576 B2 * | 7/2010 | Rothstein et al. ............... 606/41 |
| 2002/0058934 A1 | 5/2002 | Wang et al. |
| 2002/0115996 A1 | 8/2002 | Wilson et al. |
| 2002/0120316 A1 | 8/2002 | Hooven et al. |

| | | | |
|---|---|---|---|
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Chrisitian |

OTHER PUBLICATIONS

Sealy, "Direct Surgical Treatment of Arrhythmias. The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101: 584-593.

Nardella, "Radio Frequency Energy and Impedance Feedback," SPIE vol. 1068, Catheter Based Sensing and Imaging Technology (1989).

Avitall et al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:1450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99: Mar. 3, 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

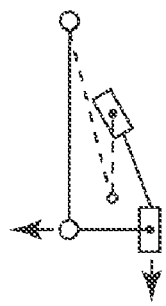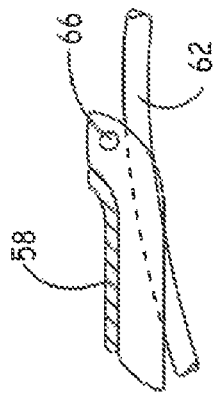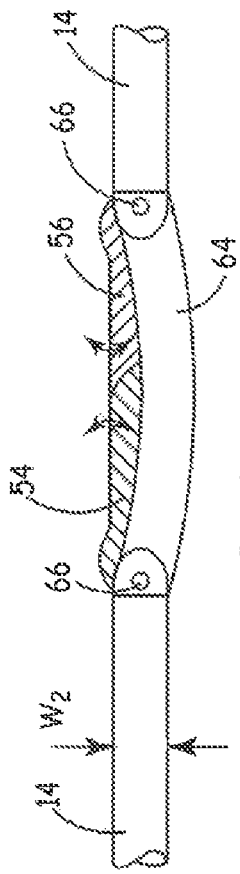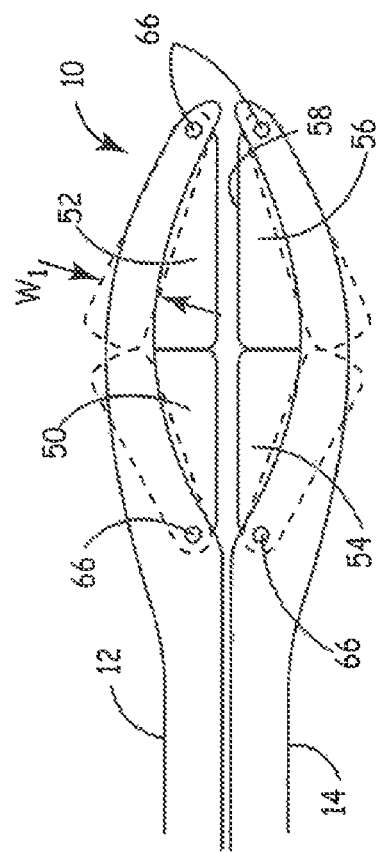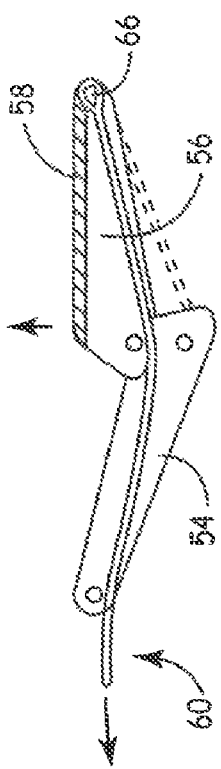
FIG. 5E
FIG. 5D
FIG. 5C
FIG. 5A
FIG. 5B

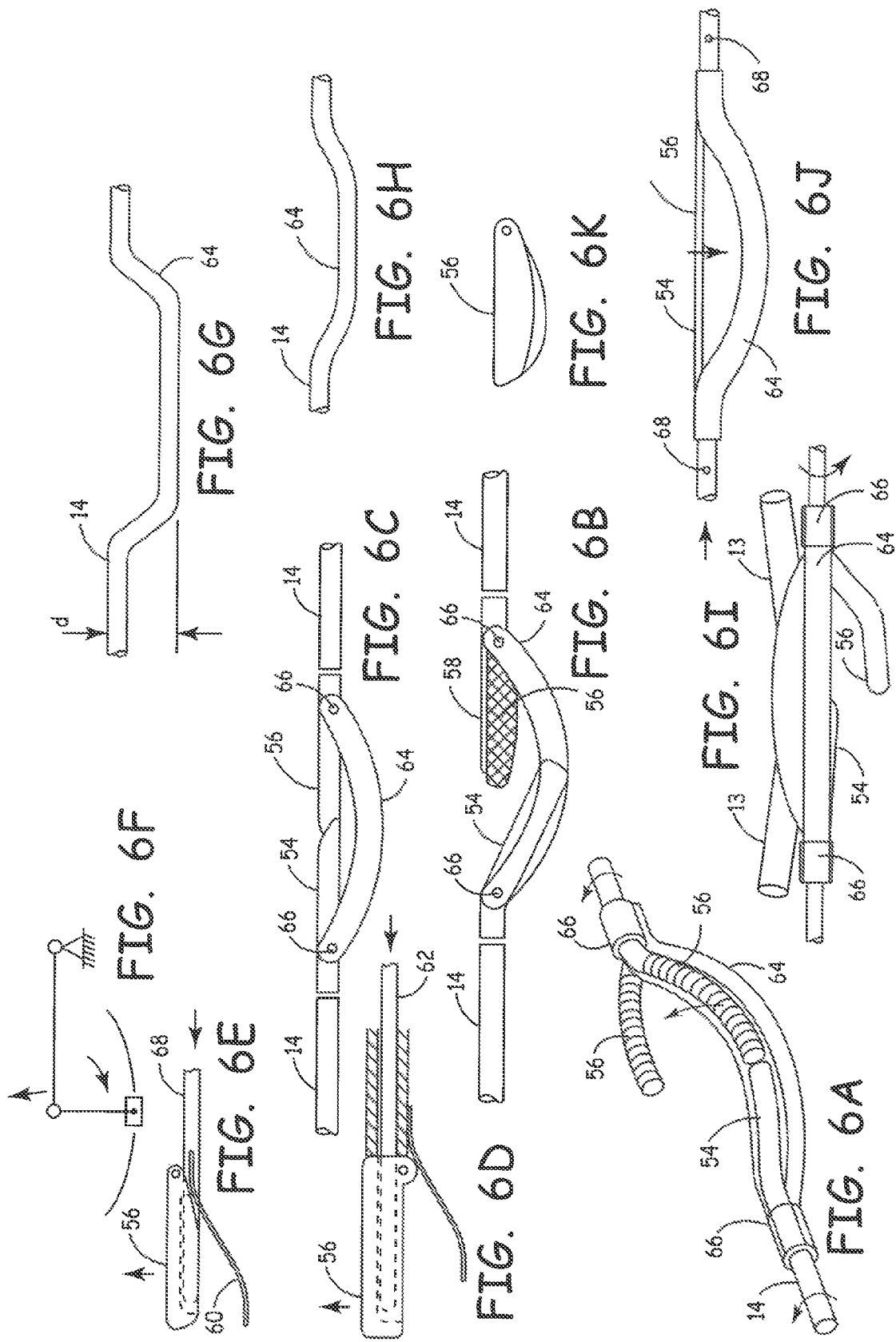

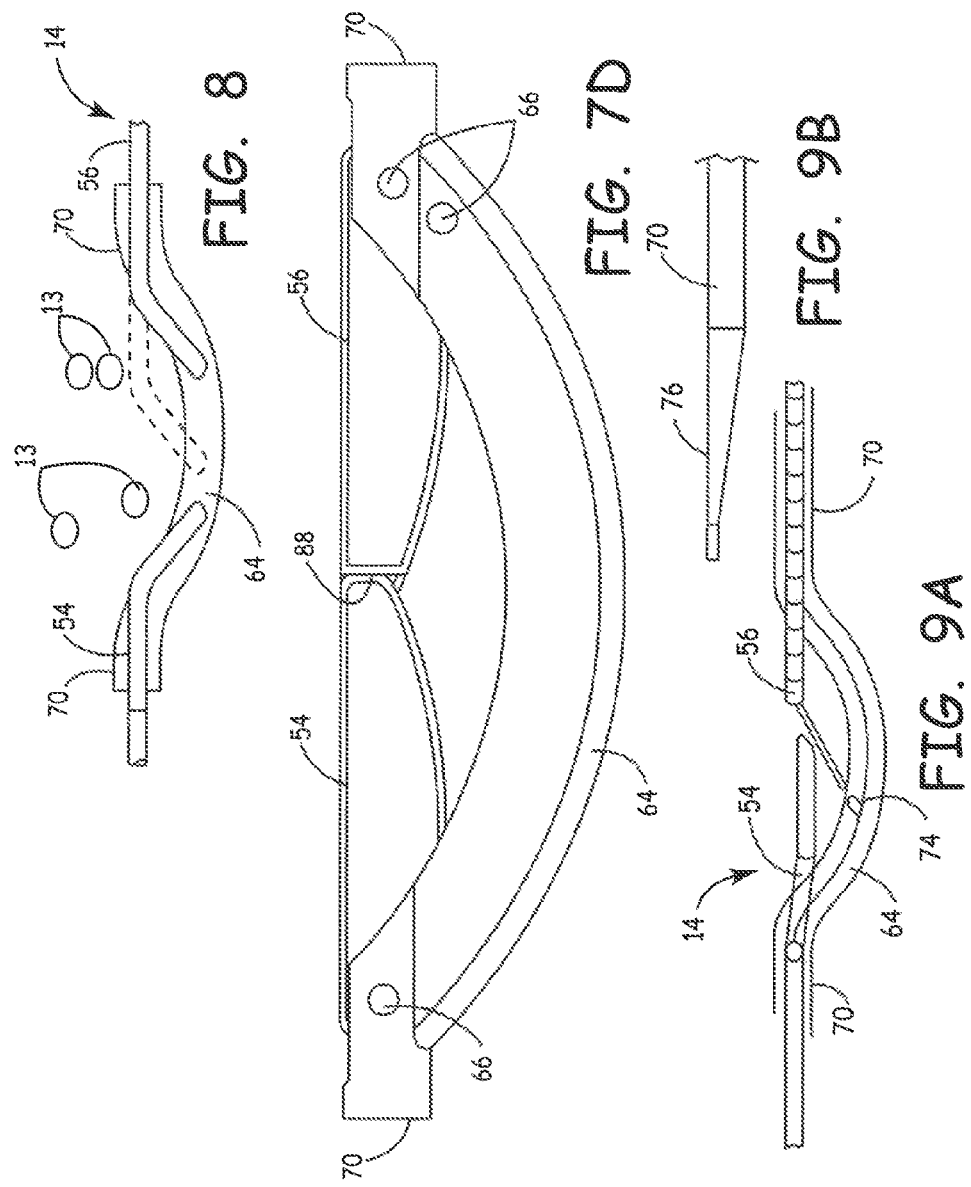

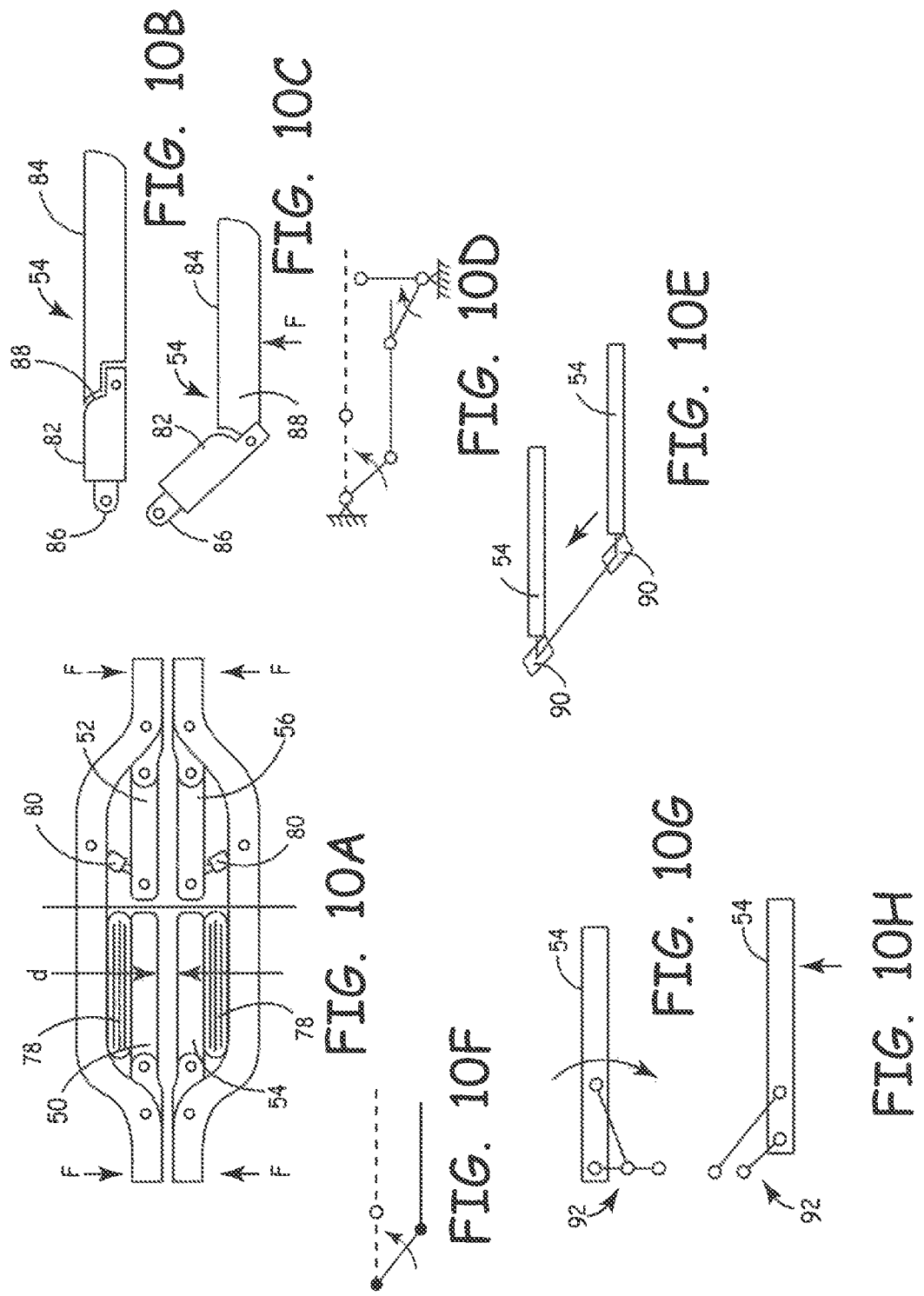

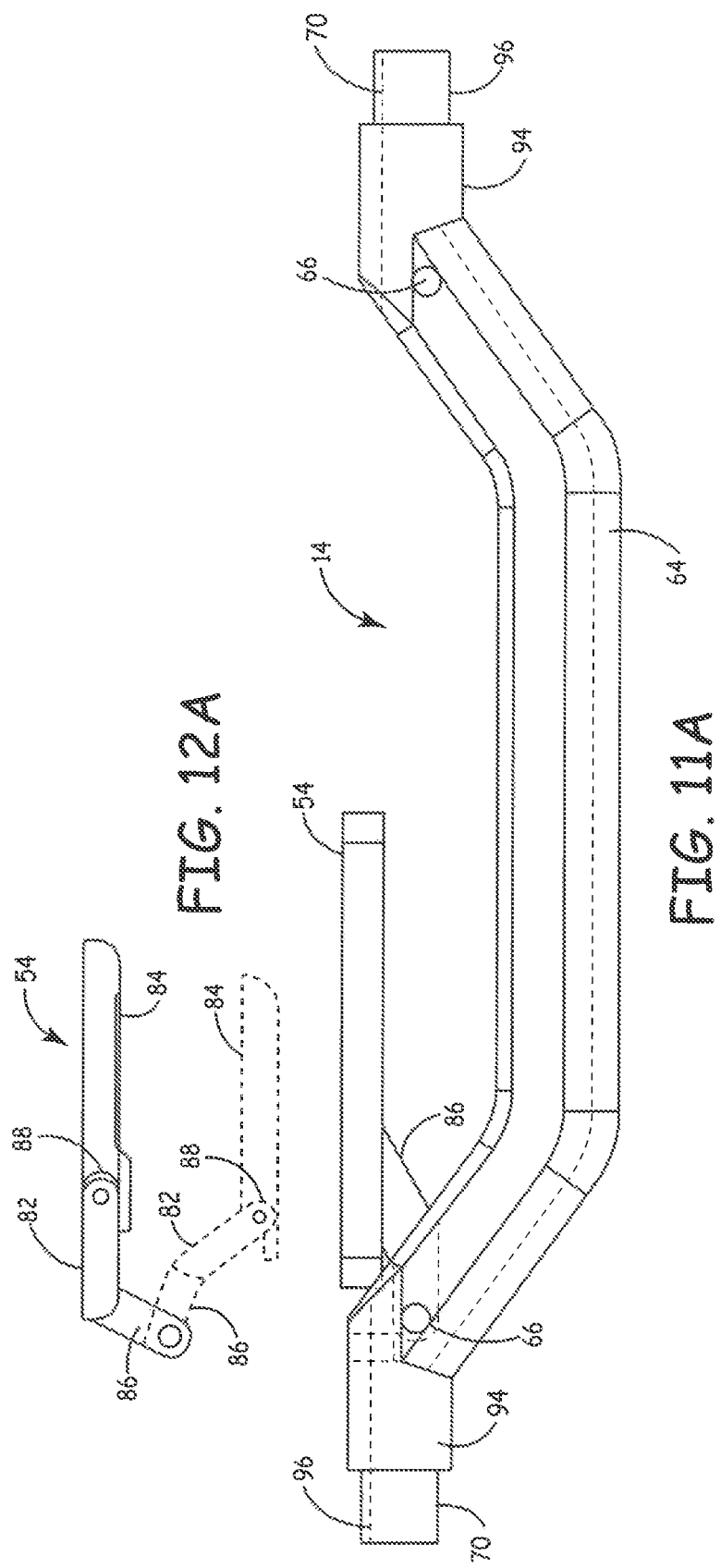

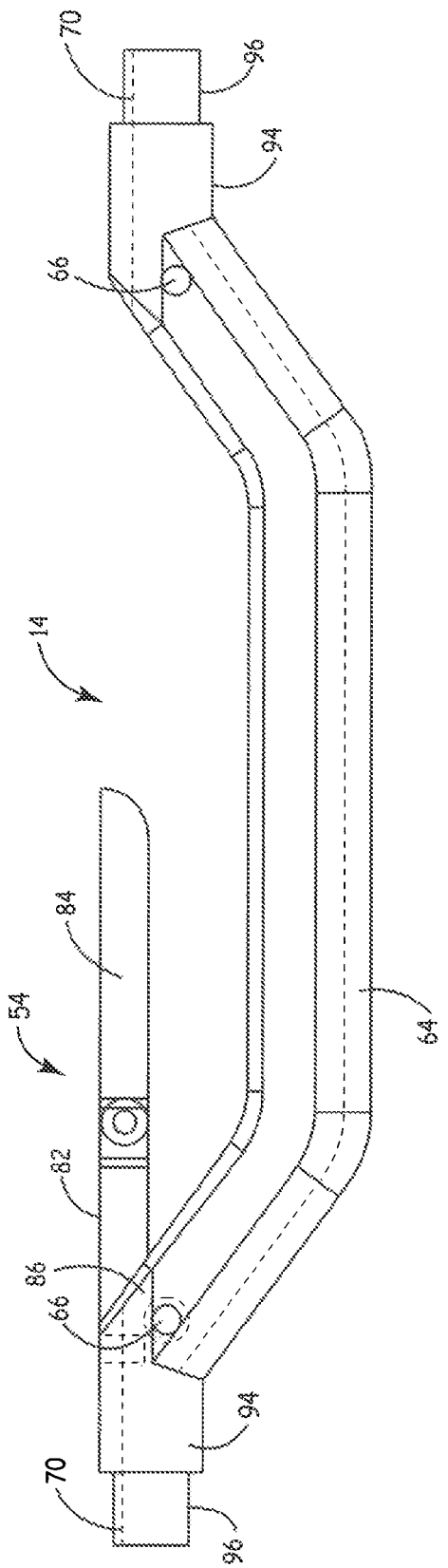

CLAMPING ABLATION TOOL AND METHOD

RELATED APPLICATIONS

This application is a divisional of U.S. patent application Ser. No. 11/143,399, filed Jun. 2, 2005, now U.S. Pat. No. 7,758,576, which application claims the benefit of the filing date of U.S. Provisional Patent Application No. 60/576,356 filed on Jun. 2, 2004, which is incorporated herein by reference in its entirety.

FIELD OF THE INVENTION

The invention is generally directed to minimally-invasive ablation of cardiac tissue.

BACKGROUND

The interest in ablation practice has been to use minimally invasive techniques to ease patient recovery. Bipolar ablation devices have been used extensively to deliver linear lesions accurately to tissue especially for the purpose of reducing the effect of atrial fibrillations.

SUMMARY OF THE INVENTION

Some embodiments of the invention provide a clamping ablation tool for ablating target tissue adjacent pulmonary veins of a patient. The clamping ablation tool can include an upper arm having an upper neck, a link assembly, and an upper actuator. The link assembly can include a distal electrode and a proximal electrode. The link assembly can be guided around the pulmonary veins. In some embodiments, the upper actuator can control movement of the link assembly. In some embodiments, the clamping ablation tool can include a lower arm that mates with the upper arm. The lower arm can include a lower neck, a distal jaw, and a lower actuator. In some embodiments, the distal jaw can include a jaw electrode, and the lower actuator can control movement of the distal jaw. In some embodiments, the upper actuator and the lower actuator can be independently operable in order to position the link assembly and the distal jaw independently. In some embodiments, the distal electrode and the proximal electrode can receive energy independently of the jaw electrode in order to allow partial blood flow through the pulmonary veins and create a continuous lesion.

In some embodiments, the clamping ablation tool can include an upper arm having an upper neck, an upper left link, an upper right link, and an upper actuator. In some embodiments, the upper left link can include a first proximal electrode and the upper right link can include a first distal electrode. The upper arm can be guided around the pulmonary veins, and the upper actuator can control movement of the upper left link and the upper right link, in some embodiments. A lower arm can mate with the upper arm. In some embodiments, the lower arm can include a lower neck, a lower left link, a lower right link, and a lower actuator. In some embodiments, the lower left link can include a second proximal electrode and the lower right link can include a second distal electrode. In some embodiments, the lower actuator can control movement of the lower left link and the lower right link. In one embodiment, the upper actuator and the lower actuator can be independently operable in order to position the upper left link and the upper right link independently of the lower left link and the lower right link. In some embodiments, the first proximal electrode and the second proximal electrode can receive energy independently of the first distal electrode and the second distal electrode in order to allow partial blood flow through the pulmonary veins and create a continuous lesion.

BRIEF DESCRIPTION OF THE DRAWINGS

FIGS. 5A-5E are side views of another embodiment of a clamping ablation tool.

FIGS. 6A-6J are side views of another embodiment of a clamping ablation tool.

FIGS. 7A-7E are perspective and side views of another embodiment of a clamping ablation tool.

FIG. 8 is a side view of another embodiment of a clamping ablation tool.

FIGS. 9A and 9B are side views of another embodiment of a clamping ablation tool.

FIGS. 10A-10H are side views of another embodiment of a clamping ablation tool.

FIGS. 11A and 11B are side and perspective views of another embodiment of a clamping ablation tool.

FIG. 12A-12F are side and perspective views of another embodiment of a clamping ablation tool.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

Figure 1:
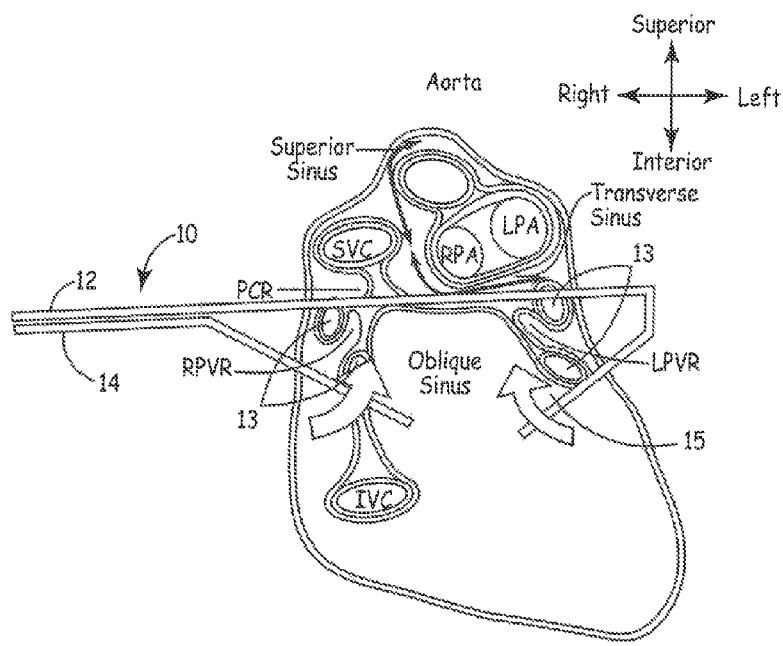
FIG. 1 is a cross-sectional view of a patient's heart with a clamping ablation tool according to one embodiment of the invention positioned around pulmonary veins.

FIG. 1 is a cross-sectional view of a patient's heart with a clamping ablation tool 10 positioned around the patient's pulmonary veins 13. The clamping ablation tool 10 can include an upper arm 12 and a lower arm 14. Some embodiments of the invention include a clamping device having two or more electrodes on a single arm, such as the upper arm 12 shown schematically in FIG. 1. The electrodes can be brought together to clamp and ablate target tissue. Some methods and devices embodying the invention provide for a single-sided approach to enter a patient's chest cavity and to manipulate jaws of an ablation tool. The ablation tool can include an articulating finger or a drawbridge-type configuration to surround and clamp onto target tissue. In some embodiments, the ablation tool can be divided into two assemblies to allow for independent placement of the electrodes in specific locations along the target tissue. After placement, the two assemblies can be joined into a single ablation tool. In some embodiments, the ablation tool can include jaws carrying the electrodes, and the jaws can clamp with respect to each other to bring the electrodes into contact with the target tissue.

Some embodiments of the invention include a two-piece ablation device with an upper arm and a lower arm that can isolate the pulmonary veins. In one embodiment, the upper arm can include a handle with an elongated neck and two or more distal links connected (e.g., by pins) at several pivot points or knuckles. The distal links can be spring-loaded with a relatively light force into a substantially straight position. In some embodiments, the distal links can only bend in one direction. One end of a cable can be attached to a middle link, routed under a short link, and through a handle. The other end of the cable can be attached to a thumb slide on the handle. In some embodiments, one long electrode can be attached to the short link and a distal end of the handle. A shorter electrode (e.g., half of the length of the long electrode) can be attached to the middle link and an end link.

Some embodiments of the invention provide a method of isolating the pulmonary veins 13 of a beating heart for the purpose of ablation, while allowing some blood flow through the pulmonary veins 13. The upper arm 12 can be used alone as a clamping device, can be modified to be a dissecting device, or can be used for monopolar ablation. A bipolar embodiment of the clamping ablation tool 10 can be used in a minimally-invasive environment (e.g., in a mini-thoracotomy or an endoscopic environment). The clamping ablation tool 10 can be designed to clamp the atrial tissue in a two-step process in order to minimize the time of complete blood flow occlusion, while ensuring a continuous lesion. Some embodiments of the invention provide a minimally-invasive approach that is less traumatic than a sternotomy. The bipolar clamping ablation tool 10 can result in a narrower lesion than the monopolar clamping ablation tool 10. The bipolar clamping ablation tool 10 can create a long continuous lesion with two ablations. In some embodiments, the clamping ablation tool 10 does not completely occlude blood flow, resulting in less trauma than with a complete occlusion. In some embodiments, the clamping ablation tool 10 never completely releases the heart, which ensures a continuous lesion. Clamping heart tissue can decrease the blood's heat sink effect.

Figure 2:
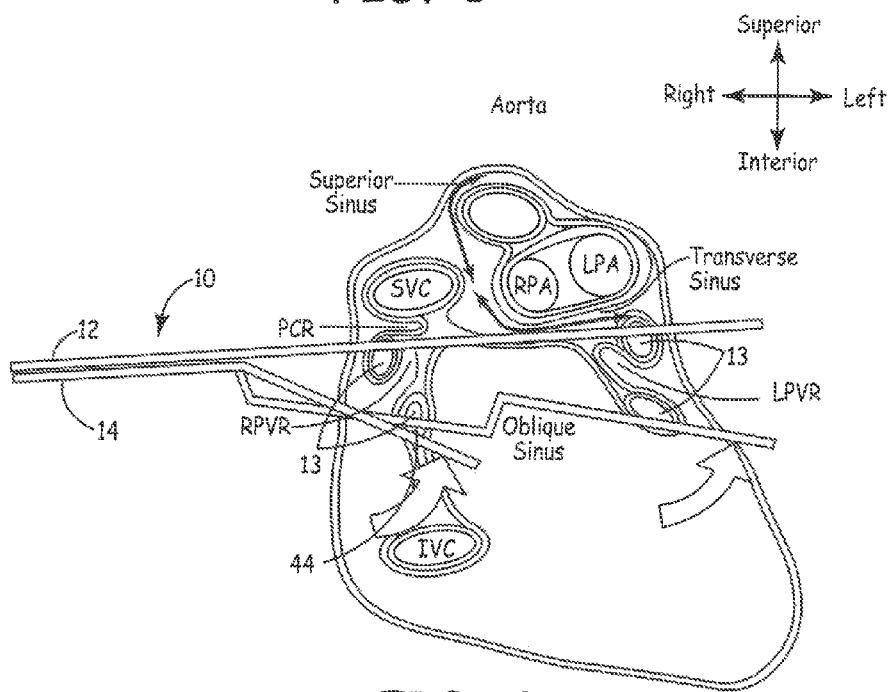
FIG. 2 is a cross-sectional view of a patient's heart with a clamping ablation tool according to another embodiment of the invention positioned around pulmonary veins.

FIG. 2 illustrates another embodiment of the clamping ablation tool 10 including a relatively straight upper arm 12 and a lower arm 14 including two or more jaws. In some embodiments, as shown schematically in FIG. 2, the ablation tool can include three jaws and three electrodes. The ablation tool can include an elongated jaw and two shorter jaws (e.g., proximal and distal lower jaws). The shorter jaws can function like a drawbridge to close one at a time or substantially simultaneously, clamping tissue against the elongated jaw. In this manner, blood flow can continue through one set of pulmonary veins, while the other set of pulmonary veins is being clamped for ablation. The lesions created by each of the two shorter jaws can be aligned to create a single long lesion for faster and more accurate ablation of the target tissue. In some embodiments, the jaws overlap to ensure a continuous lesion is created.

Individual insertion of two jaw assemblies can allow the surgeon to focus on the placement of each individual electrode, while not having to deal with the other electrodes until the ablation tool is fully assembled. Some embodiments of the ablation tool can include pins and magnets on the jaw assemblies to guide the assembly, alignment, and retention of the two jaw assemblies. In some embodiments, the jaws can be independently controlled to allow the ablation to be done in two or more steps, while preventing full occlusion of blood flow through the pulmonary veins.

Some embodiments of the invention include a clamping device with independently-separable jaws. Each jaw can be individually manipulated into the appropriate space. Once positioned, the jaws can be brought together to create a bipolar ablation device. After appropriate dissection, the separable jaws can be placed in the patient's thoracic cavity through an incision. The incision can be a thoracotomy, a sub-xyphoid incision, a sternotomy, or any other suitable incision. Ports may or may not be used to aid insertion of the jaws. A positioning device (such as the Starfish® heart positioner manufactured by Medtronic, Inc.) may or may not be used to lift, rotate, or elevate the heart. Once both jaws are appropriately positioned, the jaws can be brought together at a hinge point and assembled. Magnets, keys, accessory tools, and/or visualization techniques can be used to position and assemble the jaws. After assembly, the jaws can be closed to act as a bipolar ablation device. The jaws can be removed from the patient as an assembled unit or after disassembly.

In some embodiments, the electrodes can be positioned within a tube of a porous material to isolate the target tissue from direct contact with the ablation energy. The tubes can be constructed of a porous polymer suitable for insertion into the body and suitable for contact with tissue and blood. The porous polymer can be a "weeping" polymer capable of allowing a liquid (such as a saline) to be pumped into the tube, to surround the electrodes, and to conduct the ablation energy from the electrodes to the target tissue. The electrodes in the tube can be configured as a bipolar ablation device for creating a linear lesion on the atrium adjacent the pulmonary veins.

Figure 3A:
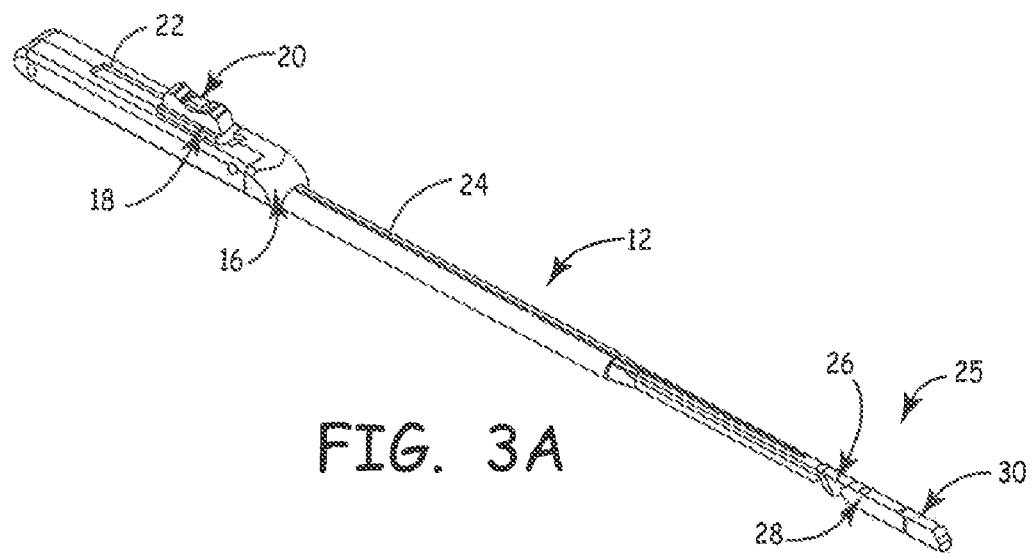
FIGS. 3A-3G are perspective views of one embodiment of a clamping ablation tool.
Figure 3B:
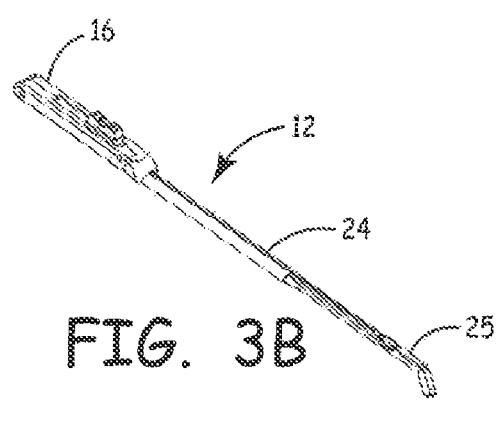
Figure 3C:
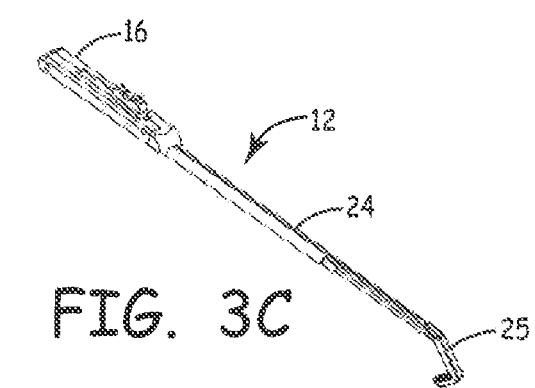
Figure 3D:
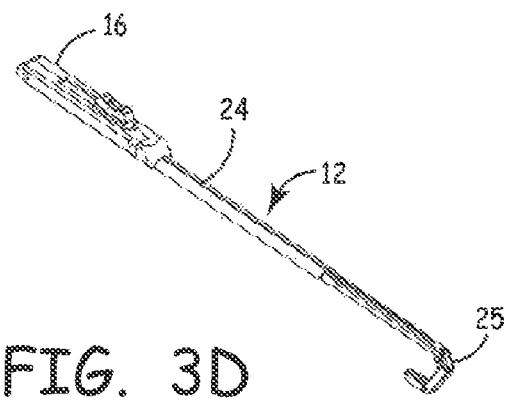
Figure 3E:
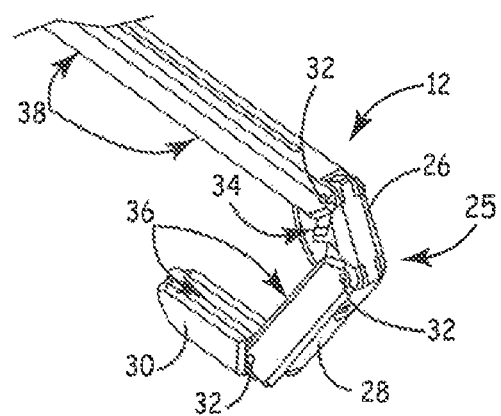
Figure 3G:
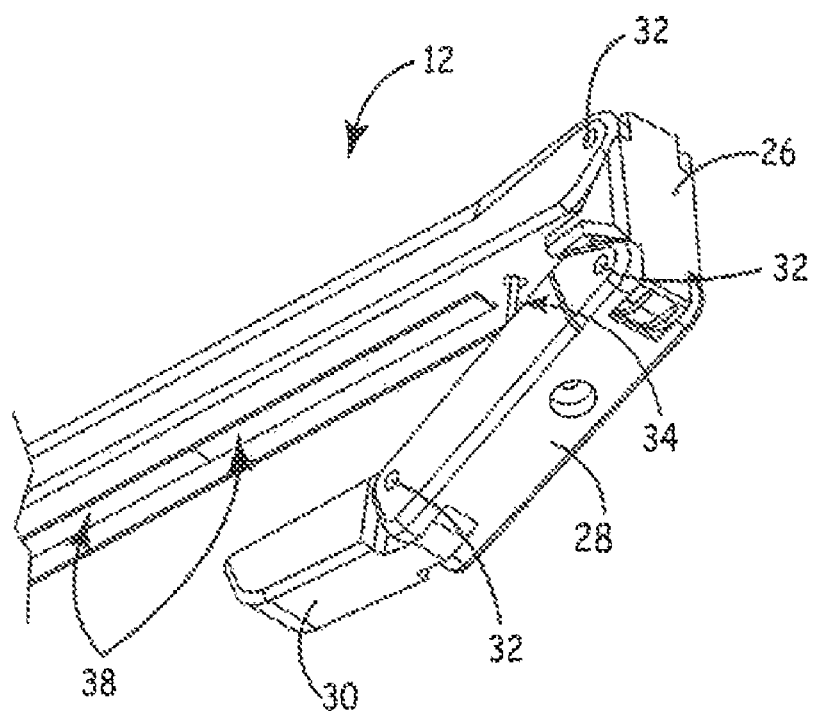

FIGS. 3A-3G illustrate one embodiment of an upper arm 12 of a clamping ablation tool 10. The upper arm 12 can include a handle 16. The handle 16 can include a thumb slide 18 and a slide release button 20 positioned within an elongated aperture 22. The upper arm 12 can also include a neck 24 and a link assembly 25. The link assembly 25, in some embodiments, can include a short link 26, a middle link 28, and an end link 30. Alternatively, link assembly 25 may include a short link 26 and a longer end link 30. As shown in FIGS. 3E and 3G, the links 26, 28, 30 can be coupled to one another with pins 32. The pins 32 can create three pivot points or knuckles. The links 26, 28, 30 can be spring-loaded substantially straight and can only bend in one direction, in some embodiments.

In the position shown in FIG. 3A, the upper arm 12 can be placed through an incision or port into the right side of the patient's chest, and then guided through the transverse sinus until the end link 30 reaches the pericardium. By gently pushing forward and slightly turning the upper handle 16, the end link 30 can naturally guide itself around the left pulmonary veins 13 and into the oblique sinus, as shown in FIGS. 3B through 3D. The upper handle 16 can be guided forward until the short link 26 is completely through the transverse sinus and up against the pericardium.

Figure 3F:
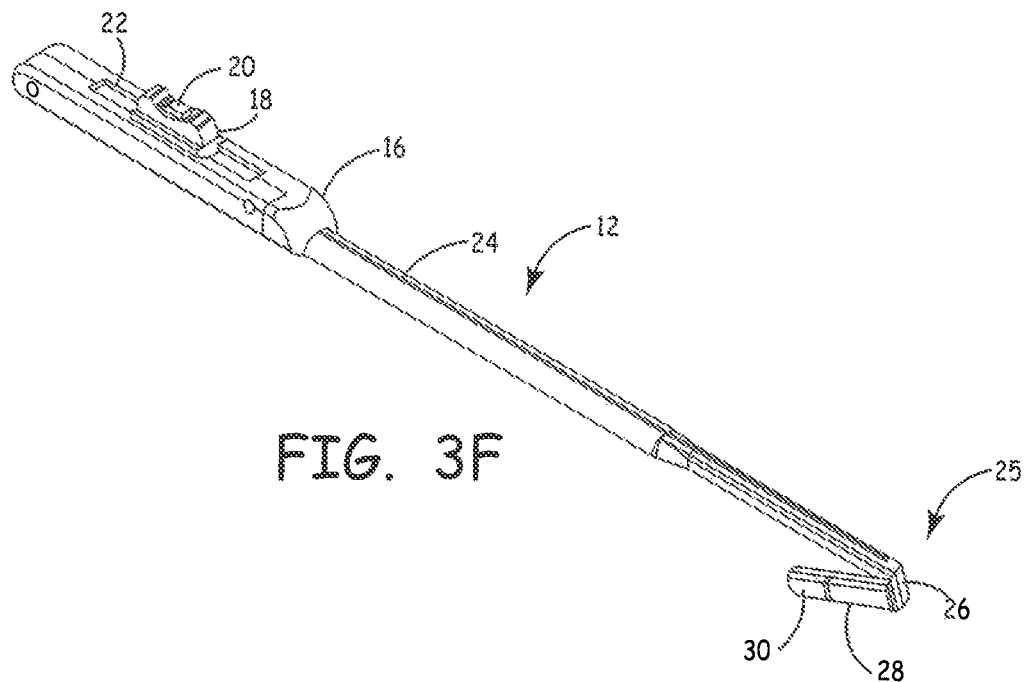

As shown in FIGS. 3E and 3G, the upper arm 12 can also include a cable 34, a distal electrode 36 and a more proximal electrode 38. Electrode 38 may comprise one continuous electrode or electrode 38 may comprise multiple shorter electrodes, e.g., two electrodes, insulated from each other, as shown in FIG. 3G. The cable 34 can be attached to the middle link 28, routed under the short link 26, through the upper handle 16, and attached to the thumb slide 18. The distal electrode 36 can be attached to the distal end of the upper handle 16 and may include a shorter electrode than the more proximal electrode 38, e.g., half the length of electrode 38. The distal electrode 36 may be a long flexible electrode, thereby allowing electrode 36 to remain continuous while attached to both the middle link 28 and the end link 30. Alternatively, distal electrode 36 may comprise multiple shorter electrodes, e.g., two electrodes, insulated from each other, thereby allowing one portion of electrode 36 to be attached to the middle link 28 and another portion of electrode 36 to be attached to the end link 30. In one embodiment, the middle link 28 may be shortened and the end link 30 configured of a sufficient length as to support the entire length of the distal electrode 36. The proximal electrode 38 can be a flexible, short electrode (e.g., half the length of the distal electrode 36). The proximal electrode 38 can be attached to the middle link 28 and the end link 30. As shown in FIG. 3F, pulling back on the thumb slide 18 can result in the middle link 28 and the end link 30 beginning to straighten and lightly clamp on the atrial tissue around the pulmonary veins 13. Rather than a thumb slide 18, the clamping ablation tool 10 can include a trigger, a torque screw, a lever, etc. to control the links 28 and 30.

FIGS. 4A-4E illustrate the clamping ablation tool 10 including both the upper arm 12 and the lower arm 14. The lower arm 14 can include a lower handle 40, a lower neck 42, and a distal jaw 44. The lower handle 40 can include a lower thumb slide 46. The distal jaw 44 can include a jaw electrode 48. The lower arm 14 can be inserted through the incision or port through which the upper arm 12 was inserted or any other suitable incision or port. The lower arm 14 can be positioned so that the distal jaw 44 is in the oblique sinus. The lower arm 14 can include a cable (not shown) that runs through the lower handle 40 and is attached to the lower thumb slide 46. The cable can actuate the distal jaw 44. In some embodiments, the jaw electrode 48 can be half the length of electrode 38 of the upper arm 12. For example, length of electrodes 36 and 48, together, may be approximately equivalent to the length of electrode 38. In one embodiment, the length of electrode 36 may be approximately equal to one portion of electrode 38 while the length of electrode 48 may be approximately equal to a separate portion of electrode 38. The two portions of electrode 38 may be insulated from each other. In one embodiment, the lower arm 14 can lock into a specific position in relation to the upper arm 12 in order to ensure the electrode tips are aligned to create a substantially continuous lesion.

Figure 4A:
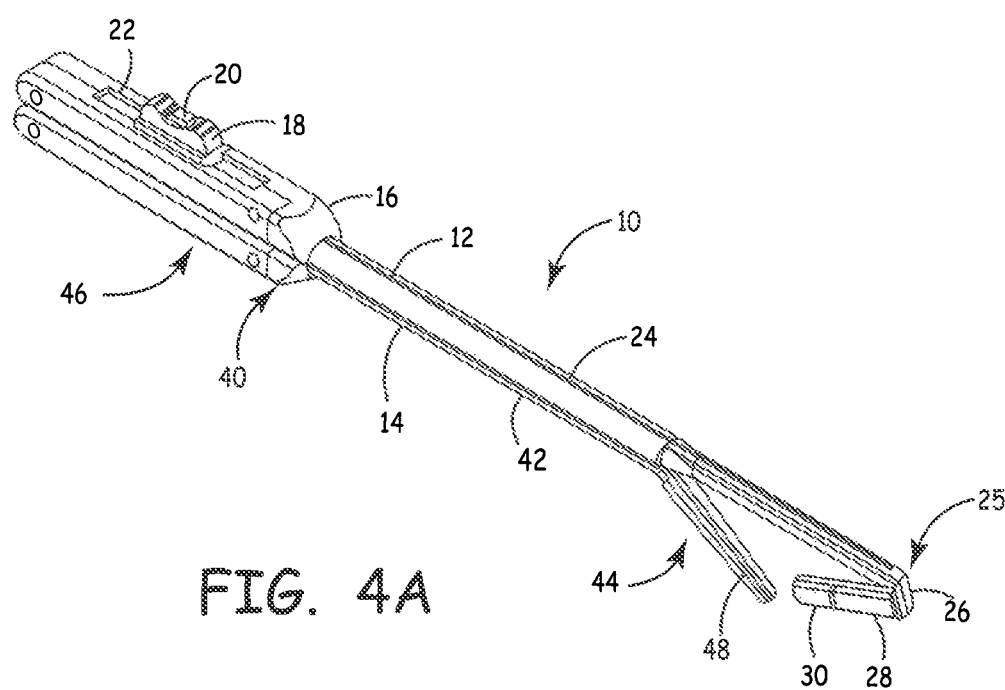
FIGS. 4A-4D are perspective views of another embodiment of a clamping ablation tool.
Figure 4B:
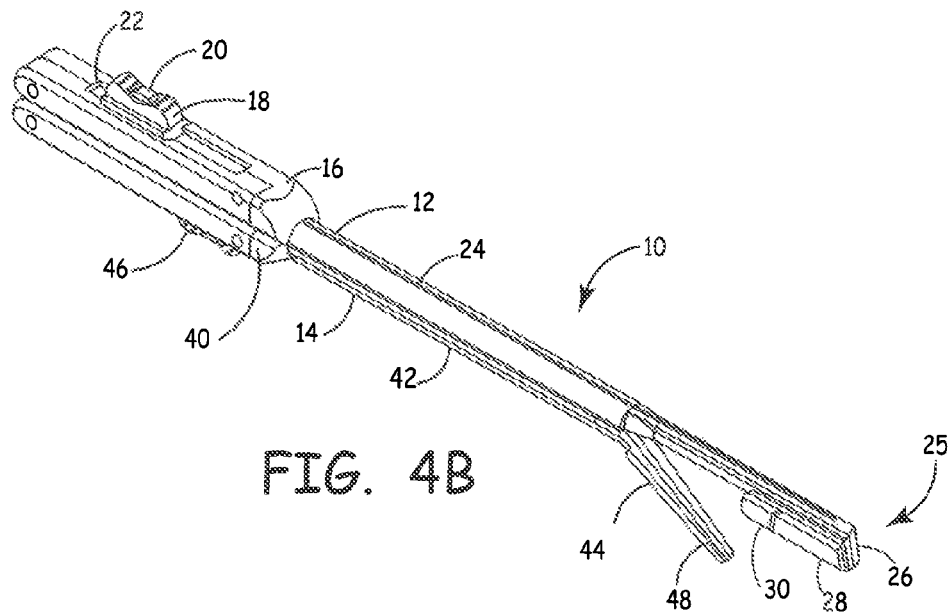

As shown in FIG. 4B, pulling back on the upper thumb slide 18 can actuate the middle link 28 and the end link 30 in order to occlude the left pulmonary veins 13. The distal jaw 44 of the lower arm 14 may not be activated in order to allow blood to continue flowing through the right pulmonary veins 13. The distal electrode 36 and the electrode 38 can be activated and the ablation can be performed with the clamping ablation tool 10 shown in the position of FIG. 4B.

Figure 4C:
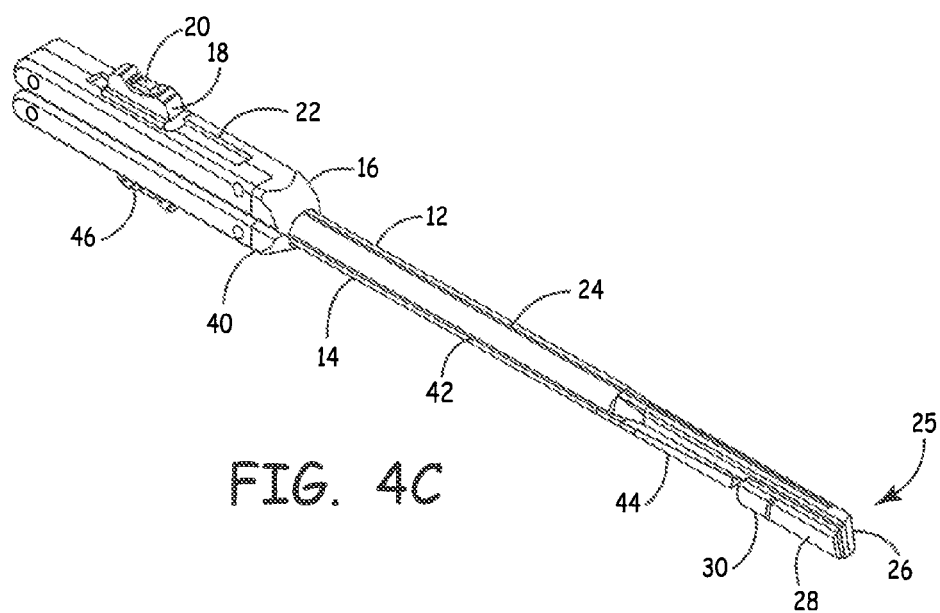
Figure 4D:
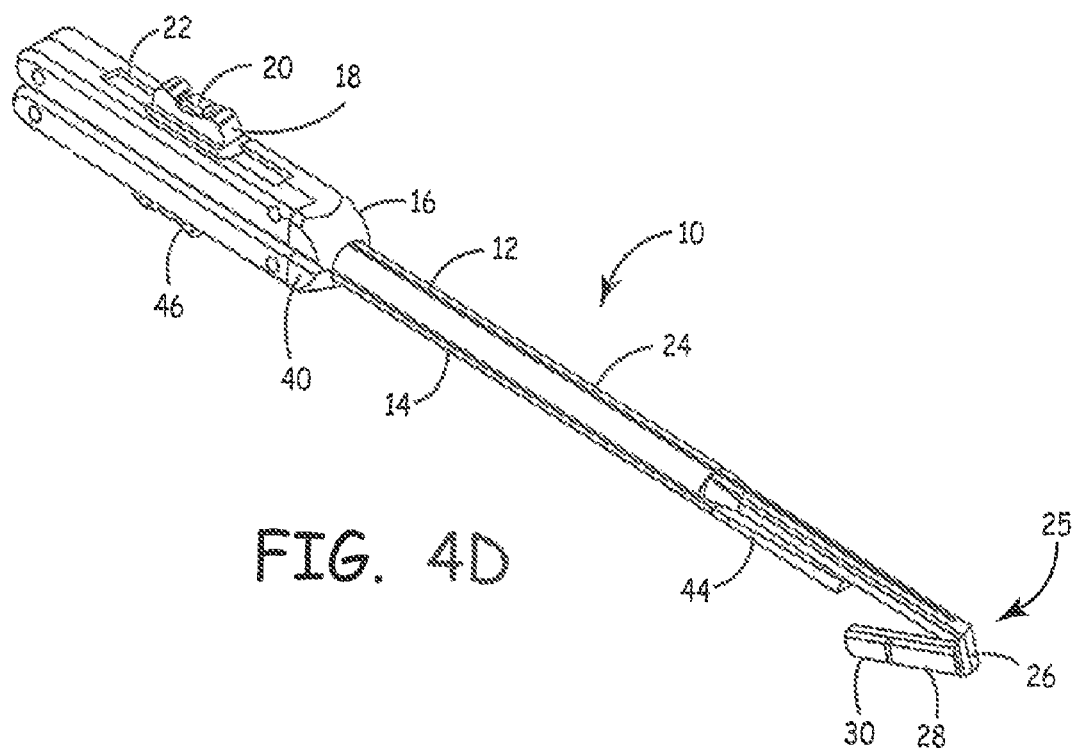

As shown in FIG. 4C, the lower thumb slide 46 on the lower arm 14 can be moved in order to actuate the distal jaw 44. In this manner, flow through the pulmonary veins 13 can be completed occluded (e.g., for a brief time period). This can ensure that the electrodes will align in order to provide a substantially continuous lesion on the atrial tissue. The distal jaw 44 can clamp the atrial tissue in the position shown in FIG. 4D. The jaw electrode 48 can be activated and the ablation can be performed. As shown in FIG. 4D, the upper thumb slide 18 can be moved as quickly as possible in order to minimize the time of complete occlusion in order to release the link assembly 25. The electrode 48 can be activated and the ablation can be performed. Once the ablation is complete, the lower thumb slide 46 can be released and the clamping ablation tool 10 can be removed in the reverse order in which it was placed within the patient.

Some embodiments of the invention can include a clamp ablation device having a shutter design. The clamp ablation device can include a rigid framework that can carry movable segments, such as shutters or beams that can be deployed in opposing sets to clamp and occlude the atrium adjacent the pulmonary veins 13. The clamping ablation tool 10 with the shutter design can be configured to clamp adjacent to the left or right pulmonary veins, either sequentially or simultaneously. Movable segments within the clamping ablation tool 10 can be actuated using linkages, rods, balloons, and bellows. Ablation electrodes can be affixed to the movable segments and can make contact with the atrium when in a deployed position. The movable segments can travel out of the plane defined by the frame of the clamping ablation tool 10 in order to extend upward into the atrium, in some embodiments. In some embodiments, the clamping ablation tool 10 with a shutter design can include separately or simultaneously deployed members to provide occlusion and carry radio frequency electrodes for atrial fibrillation therapies. The clamping ablation tool 10 can be compatible with minimally-invasive cardiac surgery techniques. The clamping ablation tool 10 can be integrated into both rigid and flexible delivery systems. The clamping ablation tool 10 can be deployed through single-sided surgical approaches. Balloon activation can be used to provide lateral displacement of surrounding tissues or structures. An open position of the clamping ablation tool 10 can provide flow through both pulmonary veins sets 13. The clamping ablation tool 10 can be a single-placement, dual-action device which does not require that the overall system be repositioned by the surgeon between right and left pulmonary vein isolation procedures. The clamping ablation tool can provide a backbone for ablation and other therapies requiring interruption of pulmonary vein flow or intermittent and controlled clamping of tissue or other structures.

FIGS. 5A-5E illustrate an embodiment of the clamping ablation tool 10 including a shutter design. The clamping ablation tool 10 can include an upper left link 50, an upper right link 52, a lower left link 54, and a lower right link 56. The upper left link 50 and the upper right link 52 can be connected to the upper arm 12 via fasteners 66. The lower left link 54 and the lower right link 56 can be coupled to the lower arm 14 with fasteners 66. The links 50, 52, 54, 56 can each include an electrode face 58. The links 50, 52, 54, 56 can include multiple positions as shown as shown in phantom in FIG. 5A. FIG. 5A also illustrates that the upper arm 12 and the lower arm 12 can each include a width $w_1$ of approximately 10 mm.

Although the configurations and connections are sometimes described herein with respect to a single link or two links, it should be understood that any of the alternative configurations and connections can be used in conjunction with any or all of the links 50, 52, 54, 56. FIG. 5B illustrates a cable or wire 60 that can be connected to the lower left link 54 and/or the lower right link 56 in order to move the links 54, 56 and their electrode faces 58. FIG. 5C illustrates an embodiment of the lower arm 14 including the lower left link 54 and the lower right link 56 each coupled via fasteners 66 to lower arm segments. The lower arm segments can be constructed of a flexible material, for example, having a width $w_2$ of approximately 8 mm. The lower arm 14 can include a clamping area section 64 that can be constructed of a substantially rigid material. In some embodiments, the lower arm 14 can include a smooth transition between the flexible lower arm segments and the rigid clamping area section 64. The links 50, 52, 54, 56 can be actuated using air and/or fluid pressure or a deflection caused by the rod 62. FIG. 5D illustrates a rod 62 that can be used to move the electrode face 58 of the links 50, 52, 54, 56. FIG. 5E illustrates the various forces placed on the links 50, 52, 54, 56 and the upper arm 12 and the lower arm 14.

FIGS. 6A-6J illustrate an embodiment of the clamping ablation tool 10 including a shutter design. FIG. 6A illustrates the lower arm 14, which can include a lower left link 54, a lower right link 56, and a clamping area section 64. The links 54 and 56 can be coupled to the lower arm 14 with fasteners 66 in the form of collars. In some embodiments, the links 54 and 56 can rotate out of a plane of the clamping area section 64, as shown in FIG. 6A. FIG. 6I is a top view of the lower arm 14 positioned with respect to the pulmonary veins 13. The lower right link 56 is shown rotated out of the plane of the lower arm 14 and the clamping area section 64. In some embodiments, the links 54 and 56 can be rotated toward an anterior portion of the patient.

FIG. 6B is a side view of the lower arm 14 including the links 54 and 56. FIG. 6B illustrates the lower left link 54 in a lower position, and the lower right link 56 in an upper position. FIG. 6C illustrates the lower left link 54 and the lower right link 56 in raised positions.

FIG. 6D illustrates one embodiment of the lower right link 56 coupled to a stiffener 68. The stiffener 68 can be extended from the lower arm 14 into the lower right link 56, or any other link. FIG. 6E also illustrates the stiffener 68 connected to the lower right link 56, along with a cable 60 that can be used to move the link 56 between its lower and upper positions.

FIG. 6F illustrates the forces that can be exerted on the links of the lower arm 14. FIG. 6G illustrates one embodiment of the clamping area section 64 including a recessed area with a diameter d. The diameter d can, in some embodiments, be approximately 10 mm. FIG. 6J also illustrates the stiffeners 68 that can be placed within the lower arm 14 and through a portion of the clamping area section 64 and into the links 54 and 56.

FIG. 6H illustrates another embodiment of the clamping area section 64 with a more shallow recessed area. FIG. 6K illustrates an embodiment of the lower right link 56 having a curvature to more closely match the framework of the clamping area section 64.

FIGS. 7A-7D illustrate another embodiment of the clamping ablation tool 10 including a shutter design. The clamping ablation tool 10 can include tubes 70 that can connect to the lower arm 14. The tubes 70 can include rectangular recesses 71 that can receive the lower left link 54 and the lower right link 56. The tubes 70 can be coupled to the clamping area section 64, which can include a curved recess 72 that can receive the end portions of the links 54 and 56. The tube 70 can be coupled to the clamping area section 64 with any suitable fasteners 66, such as pins.

Figure 7A:
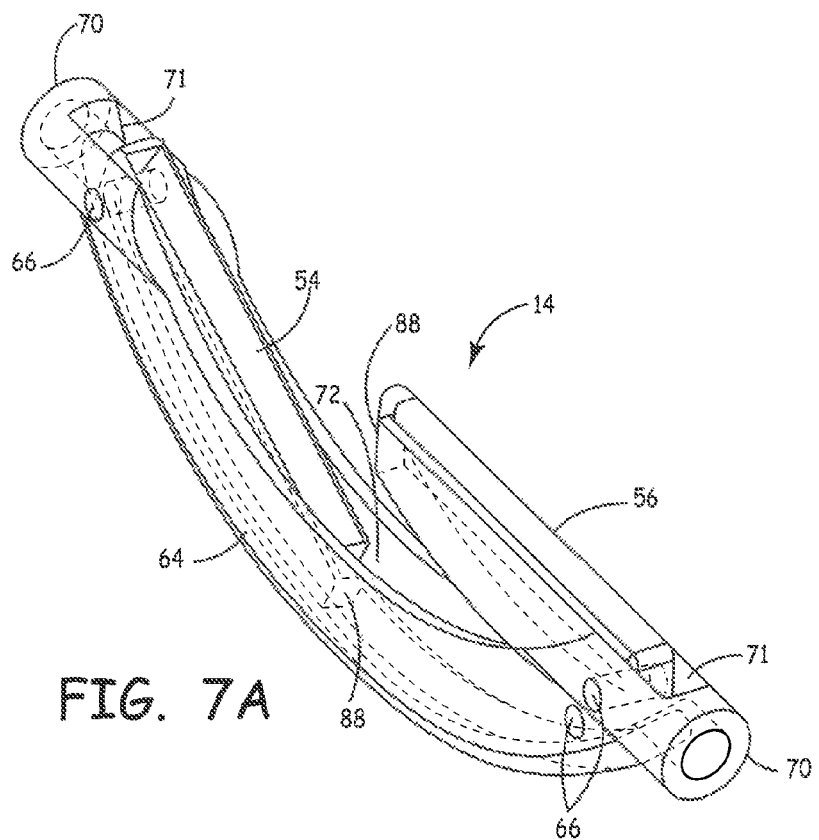
Figure 7B:
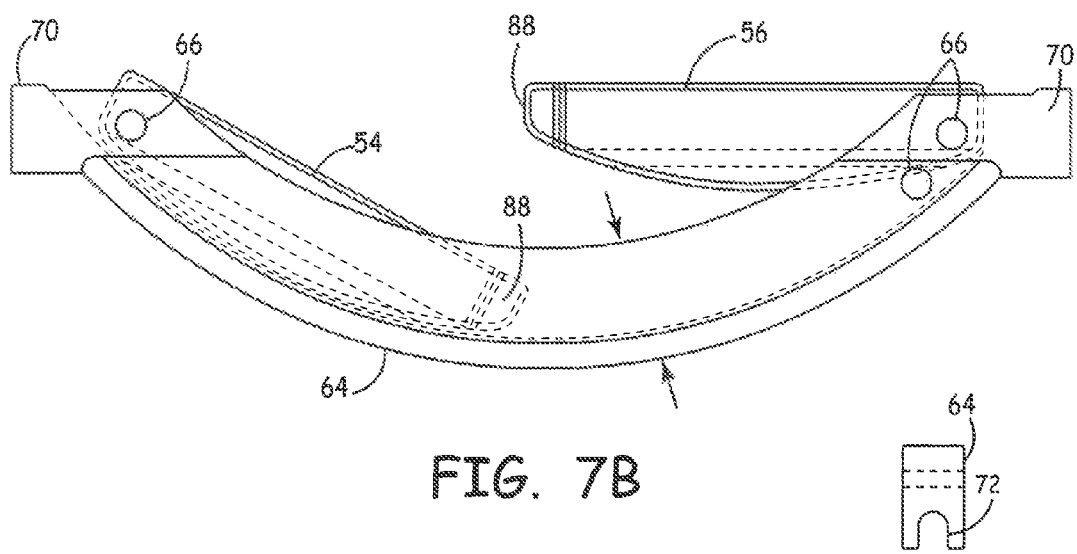
Figure 7C:
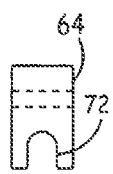
Figure 7E:
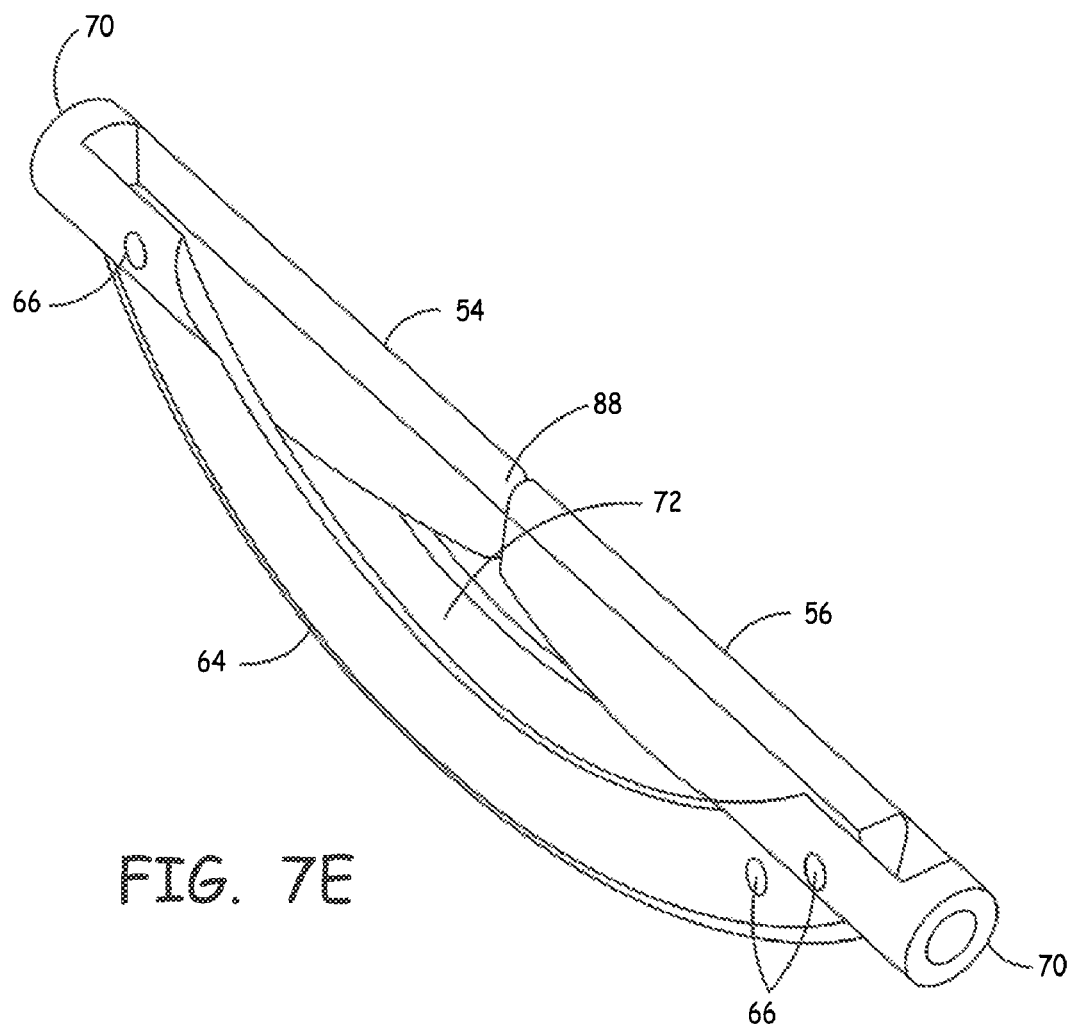

FIGS. 7A and 7B illustrate the lower left link 54 in a lower position and the lower right link 56 in an upper position. FIG. 7C illustrates a cross-sectional profile of the clamping area section 64 including the curved recess 72. FIG. 7D illustrates the lower left link 54 and the lower right link 56 in their upper positions. In some embodiments, the lower left link 54 and the lower right link 56 can include mating surfaces 88. For example, the lower right link 56 can include a recess that can mate with an end of the lower left link 54. FIG. 7E is a solid model diagram of the lower arm 14 including the lower left link 54 and the lower right link 56 in their upper positions with the mating surfaces 88 in contact.

FIG. 8 illustrates an embodiment of the lower arm 14 including a lower left link 54 and a lower right link 56 that can slide toward the pulmonary veins 13 with respect to the tubes 70. FIG. 8 illustrates the lower right link 56 in a recessed position with respect to the tubes 70 and in an extended position with respect to the tubes 70 (in phantom). The lower right link 56 can be moved along a length of the clamping area section 64.

FIGS. 9A and 9B illustrate an embodiment of the clamping ablation tool 10 including a lower right link 56 with a tapered portion 76 coupled to the tube 70. The lower right link 56 can also include a ball attachment 74 that can connect to a portion of the clamping area section 64, for example, by use of one or more magnets. In other embodiments, the ball attachment 74 can be fit within the curved recess 72 of the clamping area section 64 by a press-fit or by a friction-fit connection.

FIGS. 10A-10H illustrate an embodiment of the clamping ablation tool 10 that can use balloons 78 or cylinders 80 to position the links 50, 52, 54, 56. As shown in FIG. 10A, a balloon 78 can be inflated or deflated in order to position the upper left link 50 or the lower left link 54. Similarly, a cylinder 80 can be used to position the upper right link 52 or the lower right link 54. Balloons 78 and/or cylinders 80 can be used in order to position any one or more of the links 50, 52, 54, 56. The embodiment illustrated in FIG. 10A is only one example of the use of balloons 78 and cylinders 80. As shown in FIG. 10A, in the extended position, the links 50 and 54 can have a spaced apart distance d, which in some embodiments, can be approximately 2 mm.

FIG. 10B illustrates an embodiment of the lower left arm 54 including a first member 82 coupled to a second member 84. The first member 82 can also be coupled to a connector 86. The lower left link 54 can include a mating surfaces 88 between the first member 82 and the second member 84. The mating surfaces 88 can include a rectangular portion secured by a pin along with one or more curved portions. FIG. 10B illustrates the lower left link 54 in its fully extended position. FIG. 10C illustrates the lower left link 54 in a retracted position.

FIG. 10D illustrates examples of forces that can be exerted on the links 50, 52, 54, 56. FIG. 10E illustrates one embodiment of the lower left link 54 including a slider member 90. The slider member 90 can be used to extend and retract the lower left link 54. FIG. 10F illustrates an example of forces that can be exerted on the lower left link 54. FIGS. 10G and 10H illustrate an embodiment of the lower left link 54 including a four-bar linkage 92 that can be used to extend or retract the lower left link 54. FIG. 10G illustrates the lower left link 54 in a deployed position, and FIG. 10H illustrates the lower link 54 in a retracted position. Balloon 78 or cylinders 80 can be used in conjunction with the embodiments shown in FIGS. 10G and 10H in order to provide a force to move the four-bar linkage 92.

Figure 11B:
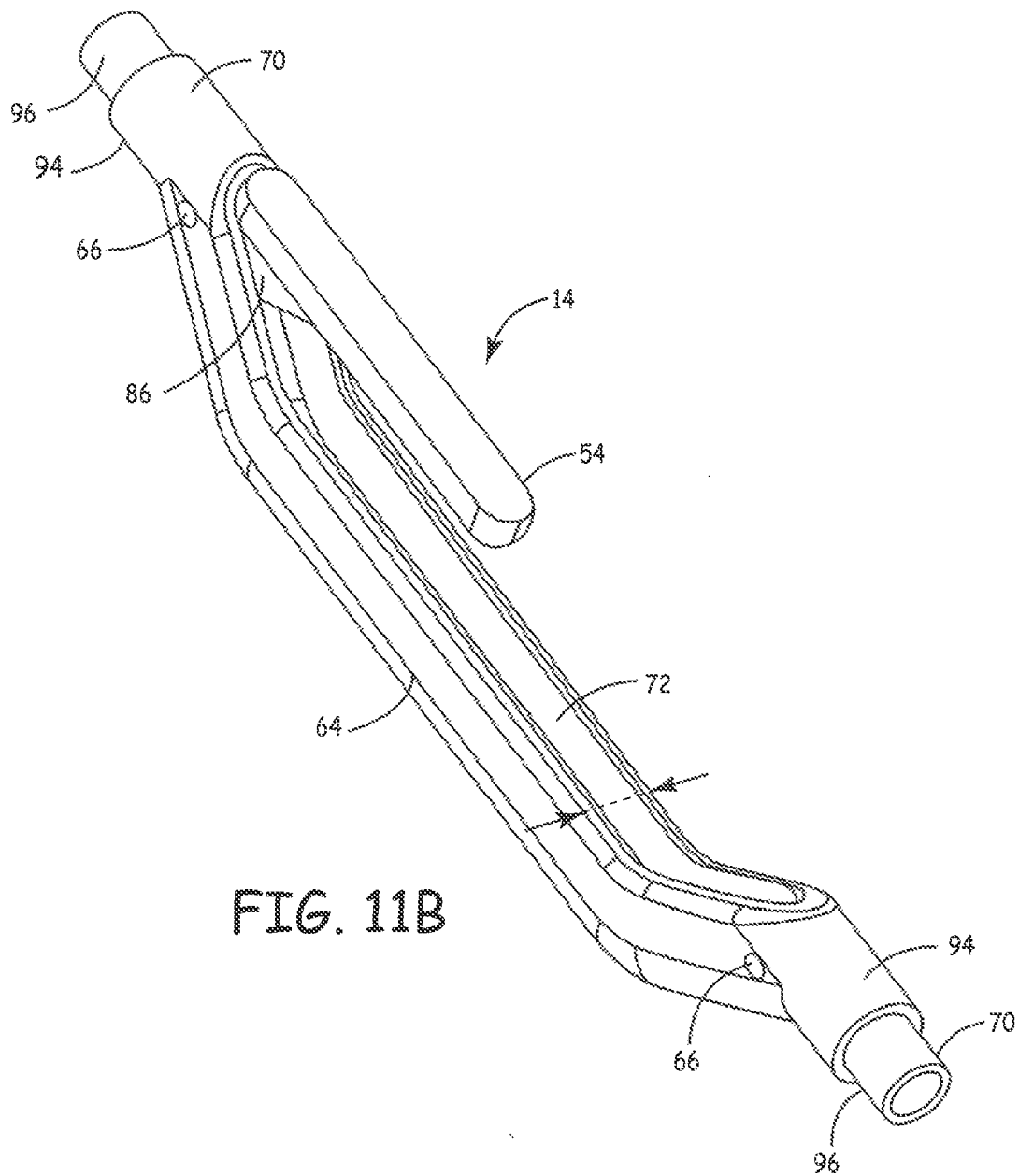

FIGS. 11A and 11B illustrate an embodiment of the lower arm 14 including the lower left link 54 with a connector 86 coupled to the clamping area section 64 with a fastener 66. Although not shown, a lower right link 56 can also be coupled to the lower arm 14 at the right portion of the clamping area section 64. The lower arm 14 shown in FIGS. 11A and 11B can also include tubes 70 with a first concentric portion 94 and a second smaller concentric portion 96. The clamping area section 64 can include a curved recess 72, as shown in FIG. 11B. The curved recess 72 can receive the lower left link 54.

Figure 12B:
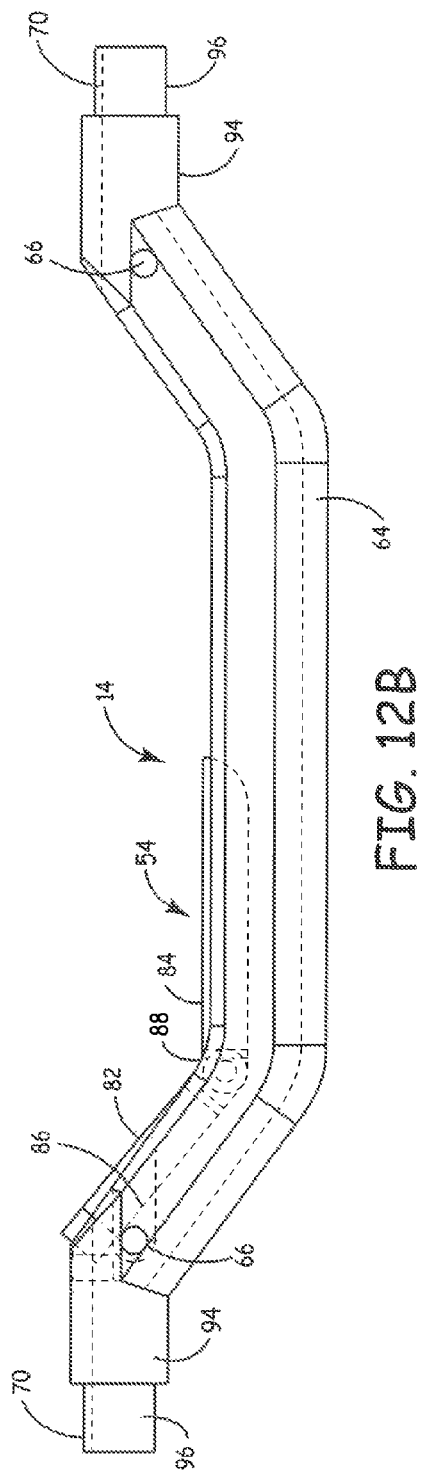

FIGS. 12A-12F illustrate an embodiment of the lower arm 14 including a two-piece lower left link 54. The lower left link 54 can include a first member 82 coupled to a second member 84. The first member 82 can include a connector 86 that can couple the lower left link 54 to the clamping area section 64 via a fastener 66. The first member 82 and the second member 84 can mate with one another in order to form mating surfaces 88, such as male and female recesses joined with a pin. FIG. 12A illustrates the lower left link 54 in an extended position, and in a retracted position (in phantom). In some embodiments, the lower left link 54 can be prevented from extending beyond the position shown in FIG. 12A as the extended position.

Figure 12C:
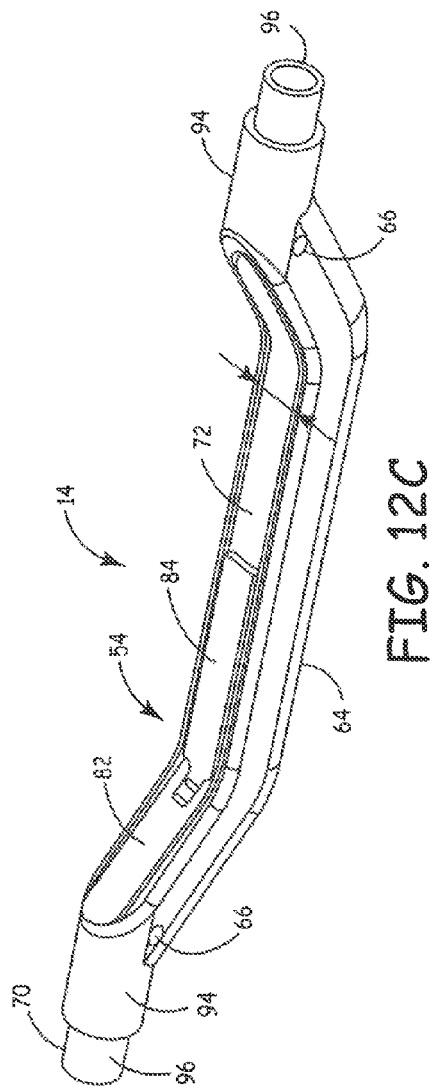
Figure 12D:
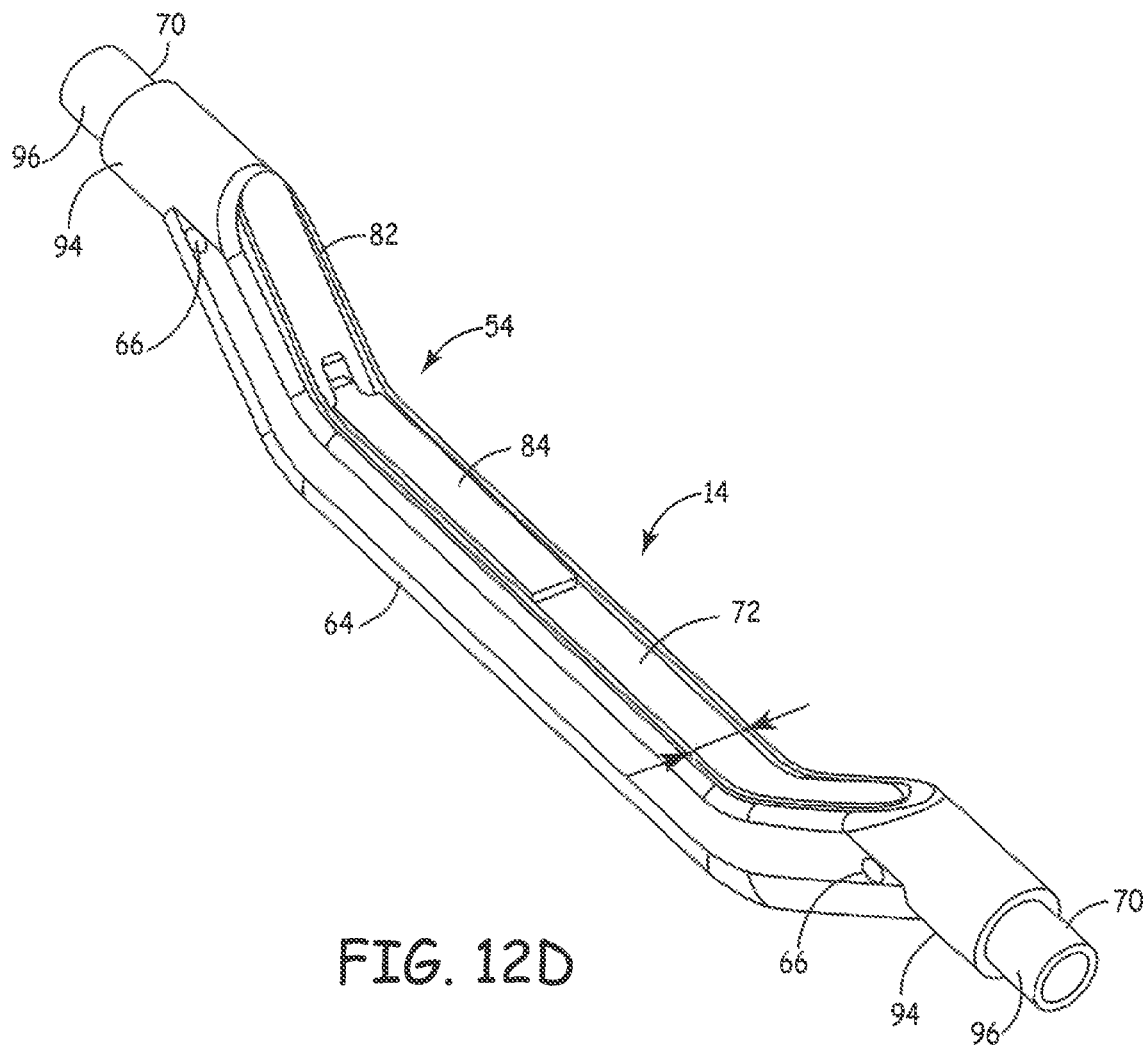
Figure 12E:
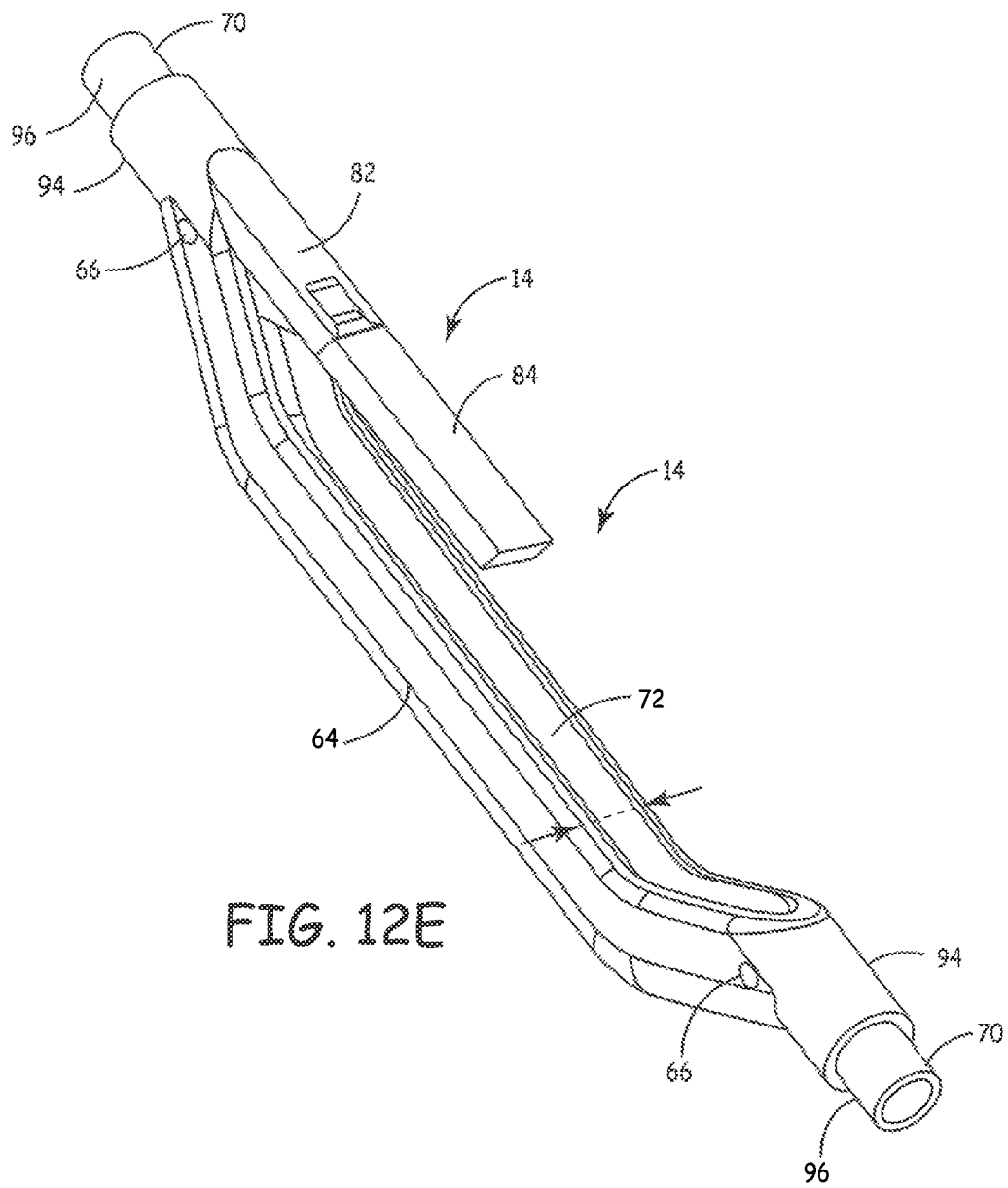

FIGS. 12B-12D illustrate the lower left link 54 in its retracted position in which it can lie within the curved portion 72 of the clamping area section 54. FIGS. 12E and 12F illustrate the lower left link 54 in its extended position in which it lies within the same plane as the tubes 70. The first and second concentric portions 94 and 96 can be used to couple the tubes 70 to another portion of the lower arm 14. Although not shown, the lower arm 14 can also include a lower right link 56. It should also be understood that the upper arm 12 can include embodiments of the link 54 being positioned in as an upper left link 50 and/or an upper right link 52.

Figure 13A:
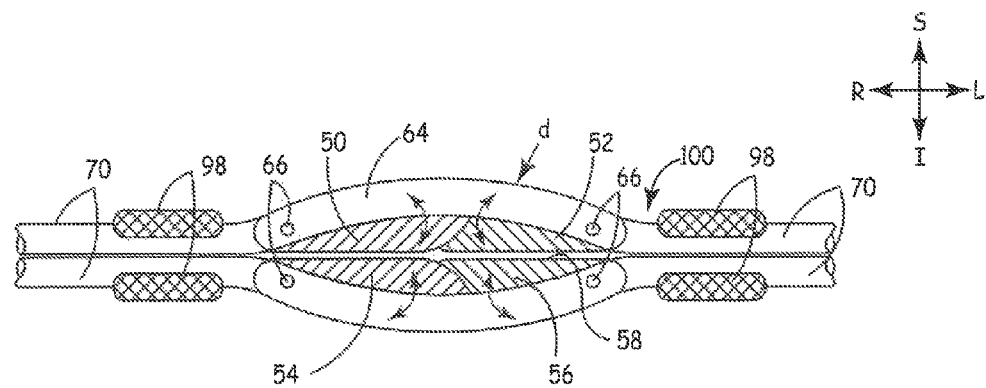
FIGS. 13A-13E are side views of another embodiment of a clamping ablation tool.
Figure 13B:
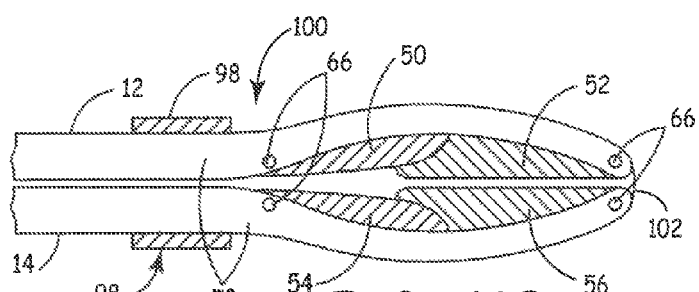

FIGS. 13A-13E illustrate an embodiment of the clamping ablation tool 10 including captures 98 coupled around the tubes 70 of the upper arm 12 and the lower arm 14. As shown in FIGS. 13A and 13B, the links 50, 52, 54, 56 can be in the form of shutters. The shutters can be grouped in a right set that can operate independently of a left set. For example, when one set of shutters is open, the other set of shutters can be closed. The links or shutters 50, 52, 54, 56 can be coupled to the tubes 70 and to the clamping area section 64 via fasteners 66. The connection between the tubes 70 and the clamping area section 64 can have a smooth transition to flow into the captures 98. In some embodiments, the clamping area section 64 is constructed of a substantially rigid material with a diameter d of less than approximately 10 mm. Each of the links or shutters 50, 52, 54, 56 can include an electrode face 58 that can contact the target tissue. The tubes 70 can be constructed of a flexible material, such as a porous polymer.

Figure 13C:
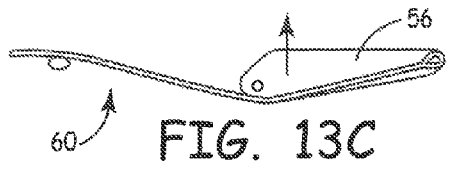
Figure 13D:
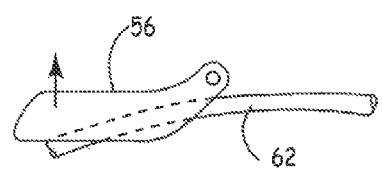
Figure 13E:

FIG. 13B illustrates another embodiment in which distal ends of the clamping area section 64 can be coupled to one another with a cable 102. As shown in FIGS. 13A and 13B, a smooth transition section 100 can be formed between the clamping area section 64 and the tube 70. FIG. 13B also illustrates that the upper left link 50 and the lower left link 54 can be positioned in a partially-open position. FIG. 13C illustrates a cable or wire 60 that can be used to hold the shutters 50, 52, 54, 56 in tension in a closed position. FIG. 13D illustrates a rod 62 that can be used as a deflector to close one or more of the shutters 50, 52, 54, 56. FIG. 13E illustrates the forces that can act on the shutters 50, 52, 54, 56 in order to actuate the shutters 50, 52, 54, 56. In other embodiments, air or fluid pressure can be use to actuate the shutters 50, 52, 54, 56.

Figure 14A:
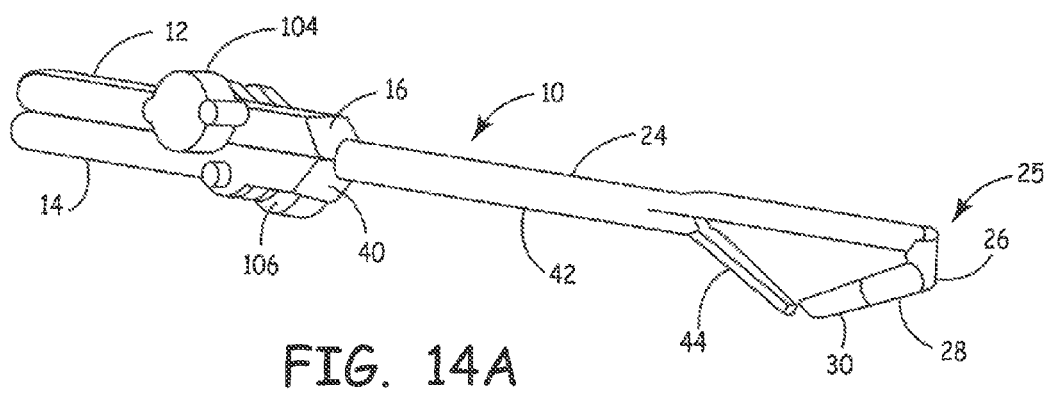
FIGS. 14A-14F are perspective views of another embodiment of a clamping ablation tool.

FIG. 2 is a schematic illustration of a clamping ablation tool 10 in the form of a compound clamp with a drawbridge design. FIGS. 14A-14F illustrate a more specific embodiment of a clamping ablation tool 10 having a drawbridge design. FIG. 14A illustrates the clamping ablation tool 10 including the upper arm 12, the lower arm 14, the upper handle 16, the lower handle 42, the upper neck 24, the lower neck 42, and the link assembly 25. The clamping ablation tool 10 can include an upper rotary control 104 and the lower rotary control 106. The clamping ablation tool 10 can include a distal jaw 44 that can interact with the link assembly 25. The link assembly 25 can include the short link 26, the middle link 28, and the end link 30. The upper arm 12 can be inserted into the patient separately from the lower arm 14.

Figure 14B:
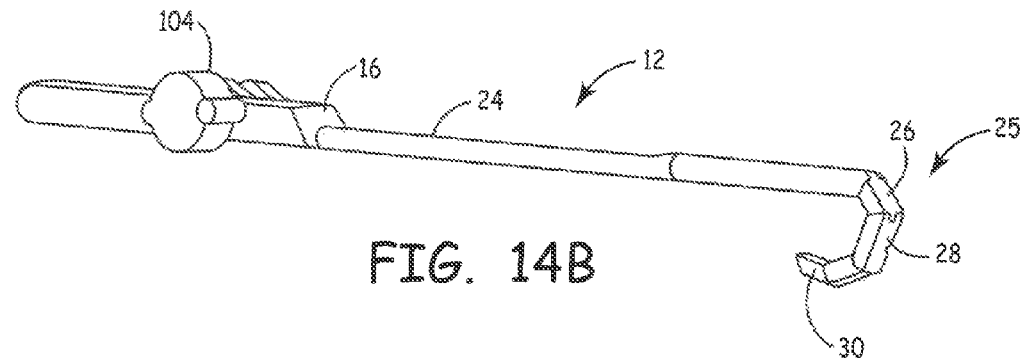
Figure 14C:
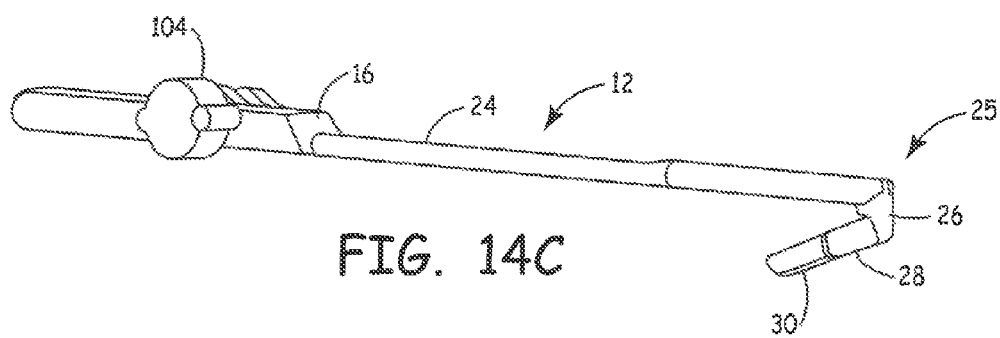
Figure 14D:
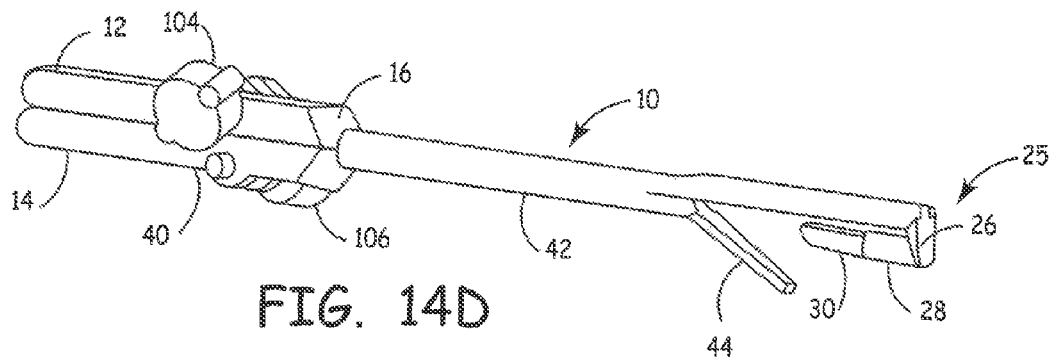
Figure 14E:
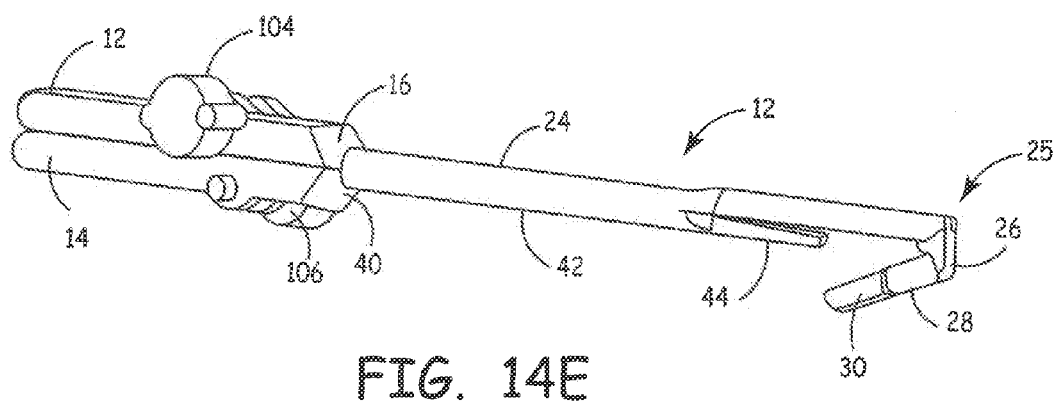
Figure 14F:
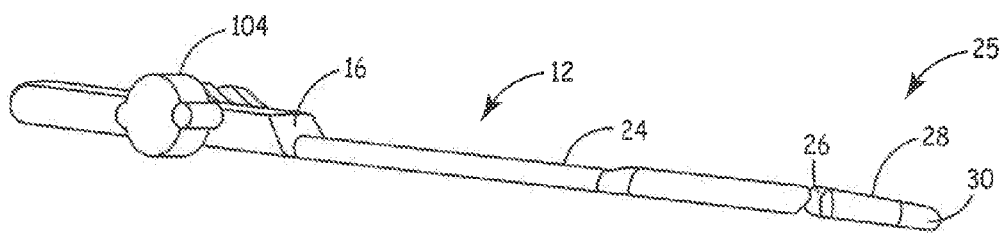

As shown in FIGS. 14B through 14C, the upper arm can be first inserted from a right thoracotomy into the patient. The lower arm 14 can then also be inserted into the right thoracotomy into the patient in order to mate with the upper arm 12, as shown in FIGS. 14D and 14E. FIG. 14F illustrates the upper arm 12 in its position before insertion into the patient or its final position while being withdrawn from the patient.

Various additional features and advantages of the invention are set forth in the following claims.

The invention claimed is:

1. A clamping ablation tool for ablating target tissue adjacent pulmonary veins of a patient, the clamping ablation tool comprising:
    a first arm including a first neck portion, a first link movably coupled to the first neck portion, and a first actuator, the first link including a first electrode, the first arm capable of being guided around the pulmonary veins, the first actuator controlling movement of the first link; and
    a second arm that is operatively connectable with the first arm, the second arm including a second neck portion, a second link movably coupled to the second neck portion, and a second actuator, the second link including a second electrode, the second arm capable of being guided around the pulmonary veins, the second actuator controlling movement of the second link;
    the first actuator and the second actuator being independently operable in order to move and position the first link independently of the second link while the first and second arms are operatively connected so as to be substantially non-movable with respect to one another;
    the first electrode and the second electrode adapted to receive energy independently of one another in order selectively create proximal and distal lesion. portions on the target tissue adjacent to the pulmonary veins.

2. The clamping ablation tool of claim 1, wherein at least one of the first and second actuators includes a thumb slide, a rotary control, a trigger, a torque screw or a lever.

3. The clamping ablation tool of claim 1, wherein at least one of the first and second links is coupled to at least one of a cable, a wire, or a rod.

4. The clamping ablation tool of claim 1, further comprising a stiffener coupled to at least one of the first arm and the second arm.

5. The clamping ablation tool of claim 1, wherein the first arm further includes a third link movably coupled to the first neck portion opposite the first link.

6. The clamping ablation tool of claim 5, wherein the third link includes a third electrode.

\* \* \* \* \*